US008729024B2

(12) United States Patent
Stracher et al.

(10) Patent No.: US 8,729,024 B2
(45) Date of Patent: May 20, 2014

(54) TARGETED DELIVERY OF PHARMACEUTICAL COMPOUNDS

(75) Inventors: Alfred Stracher, Roslyn, NY (US); Leo Kesner, West Orange, NJ (US); Abraham Shulman, Hollis Hills, NY (US)

(73) Assignee: The Resesarch Foundation of State University of New York, Albany, NY (US)

( * ) Notice: Subject to any disclaimer, the term of this patent is extended or adjusted under 35 U.S.C. 154(b) by 1031 days.

(21) Appl. No.: 12/280,844

(22) PCT Filed: Feb. 28, 2007

(86) PCT No.: PCT/US2007/062982
§ 371 (c)(1),
(2), (4) Date: Mar. 4, 2009

(87) PCT Pub. No.: WO2007/101252
PCT Pub. Date: Sep. 7, 2007

(65) Prior Publication Data
US 2009/0227522 A1    Sep. 10, 2009

Related U.S. Application Data

(60) Provisional application No. 60/777,599, filed on Feb. 28, 2006.

(51) Int. Cl.
*A61K 38/04* (2006.01)
(52) U.S. Cl.
USPC ........................................................ 514/17.7
(58) Field of Classification Search
None
See application file for complete search history.

(56) References Cited

U.S. PATENT DOCUMENTS

| 5,008,288 | A | 4/1991 | Stracher et al. | |
| 2004/0063628 | A1* | 4/2004 | Piccariello et al. | 514/12 |
| 2005/0004177 | A1 | 1/2005 | Roark | |
| 2006/0024317 | A1 | 2/2006 | Boyd et al. | |

FOREIGN PATENT DOCUMENTS

| WO | WO2005/124563 | 12/2005 |
| WO | PCT/US07/62982 | 10/2007 |

OTHER PUBLICATIONS

Definition of 'residue' retrieved from http://www.merriam-webster.com/medical/residue on Aug. 16, 2012 3 pages.*
Erokhin ('Water structure and supergigahertz phonons' Journal of Russian Laser Research v23(4) 2002 pp. 369-380).*
S.-A. Cryan, "Carrier-based Strategies for Targeting Protein and Peptide Drugs to the Lungs," AAPS Journal, Mar. 2005, pp. E20-E-41, vol. 7, No. 1.
J. Gafni et al., "Inhibition of Calpain Cleavage of Huntingtin Reduces Toxicity," The Journal of Biological Chemistry, May 2004, pp. 20211-20220, vol. 279, No. 19.
P. Warne et al., "Is There a Best Strategy for Drug Discovery?" Society for Medicines Research, Oct. 2003, pp. 1-16, vol. 10.
Supplementary Search Report for EP 07757643 dated Jul. 20, 2009.
T.R. Belliotti et al., "Structure-Activity Relationships of Pregabalin and Analogues that Target the α2-δ Protein," Journal of Medicinal Chemistry, Apr. 2005, pp. 2294-2307, vol. 48.
S.K. Ray et al., "Calpain and Its Involvement in the Pathophysiology of CNS Injuries and Diseases: Therapeutic Potential of Calpain Inhibitors for Prevention of Neurodegeneration," Current Drug Targets, CNS & Neurological Disorders, Jun. 2003, pp. 173-189, vol. 2, No. 3.

* cited by examiner

*Primary Examiner* — James H Alstrum Acevedo
*Assistant Examiner* — Ronald Niebauer
(74) *Attorney, Agent, or Firm* — Ryan, Mason & Lewis, LLP

(57) ABSTRACT

Techniques are provided for targeting a pharmaceutically active compound using, as a carrier, a molecule (or molecules) having greater affinity for a particular site in a living organism's body than for other sites therein. A compound of the formula B-L-A is provided, where B represents the residue of a small synthetic molecule, preferably one that is approved for human use, having a greater affinity for a particular site in a patient's body than for other sites in the patient's body, L represents a direct bond or a linking group, and A represents the residue of a pharmaceutically active compound.

2 Claims, 2 Drawing Sheets

STRIATAL LESION VOLUME IN 3-NP RAT MODEL
3-NP TREATMENT 50Mg/Kg/DAY BY MINIPUMP FOR 5 DAYS
GABADUR 10Mg/RAT/DAY

| RAT # | ESTIMATED VOLUME (mm3) | COEFFICIENT OF ERROR |
|---|---|---|
| SALINE 1 | 31.7 | 0.03 |
| SALINE 2 | 28.8 | 0.04 |
| SALINE 3 | 22.7 | 0.04 |
| SALINE 4 | 27.4 | 0.03 |
| GABADUR | 14.4 | 0.04 |
| GABADUR | 10.2 | 0.04 |
| GABADUR | 18.2 | 0.05 |
| GABADUR | 12.2 | 0.06 |

SUMMARY

| | MEAN | SEM |
|---|---|---|
| SALINE | 27.65 | 1.9 |
| GABADUR | 13.65 | 2.4 |

STRIATAL LESION VOLUME

TARGETED DELIVERY OF PHARMACEUTICAL COMPOUNDS

CROSS-REFERENCE TO RELATED APPLICATION(S)

This application claims the benefit of U.S. Provisional Application Ser. No. 60/777,599, filed on Feb. 28, 2006, the disclosure of which is incorporated by reference herein.

FIELD OF THE INVENTION

The present invention relates generally to delivery of pharmaceutical compounds, and more particularly relates to targeted delivery of pharmaceutical agents and/or other compounds in vivo.

BACKGROUND OF THE INVENTION

Many pharmaceutical compounds, such as, for example, antiviral, immunosuppressive, and cytotoxic cancer chemotherapy agents, generally have undesirable toxic effects on normal tissues. Such effects, which include damage to bone marrow (with consequent impairment of blood cell production) and gastrointestinal mucosa, alopecia, nausea, etc., limit the dose of a pharmaceutical compound that can be safely administered and thereby reduce the potential efficacy of the pharmaceutical compound.

Targeted drug delivery is an important objective of pharmaceutical research and development. In principle, drug targeting involves directing high concentrations of a pharmacological agent at the pathophysiologically relevant site. If successful, the result of the drug targeting would be a significant reduction in drug toxicity at other sites, thus permitting a reduction of the drug dose, and increased treatment efficacy.

Physical drug targeting approaches have focused on implanting a drug delivery device at or around the target site (for example, organ or tissue). This kind of physical targeting, such as the delivery of pilocarpine to the eye from a polymeric device, has achieved only limited success. Moreover, such a drug delivery methodology is undesirably invasive. Known biological targeting approaches, based on antibodies, in theory, could result in a highly desirable delivery profile. However, there are a number of problems related to the actual distribution of an antibody-drug conjugate in the body that have prevented researchers from achieving any real success. Additionally, biological targeting approaches involving modification of a pharmaceutical compound to have greater affinity for a particular site in a patient's body.

Accordingly, there exists a need for a more effective mechanism of delivering pharmaceutical agents and/or other compounds in vivo that does not suffer from one or more of the problems exhibited by conventional pharmaceutical compound delivery methodologies.

SUMMARY OF THE INVENTION

The present invention meets the above need by providing, in an illustrative embodiment thereof, techniques for targeting a pharmaceutically active compound using, as a carrier, a molecule (or molecules) having greater affinity for a particular site in a living organism's body than for other sites therein. Ideally, the molecules used as carriers to which the pharmaceutically active compound (for example, protease inhibitor) is attached are pharmaceutical agents or their analogs that are already known to be selectively taken up in certain tissues in the body of a patient for treatment of the patient. The targeted delivery methodology of the invention advantageously increases the efficacy of a particular treatment, without invasive surgery and/or significant clinical analysis and the associated delays of making the compound commercially available.

In accordance with one aspect of the invention, a compound of the formula (I) is provided:

$$B\text{-}L\text{-}A \quad (I)$$

where B represents the residue of a small synthetic molecule, preferably one that is approved for human use, having a greater affinity for a particular site in a patient's body than for other sites in the patient's body, L represents a direct bond or a linking group, and A represents the residue of a pharmaceutically active compound (for example, protease inhibitor).

In accordance with another aspect of the invention, a method of targeting a pharmaceutically active compound to a particular site in a patient's body includes the steps of coupling the pharmaceutically active compound to a small synthetic molecule having greater affinity for the particular site than for other sites in the patient's body, and administering a therapeutically effective amount of the coupled compound to the patient.

A more complete understanding of the present invention, as well as further features and advantages of the present invention, will become apparent from the following detailed description of illustrative embodiments thereof.

DETAILED DESCRIPTION OF THE INVENTION

Figure 1:
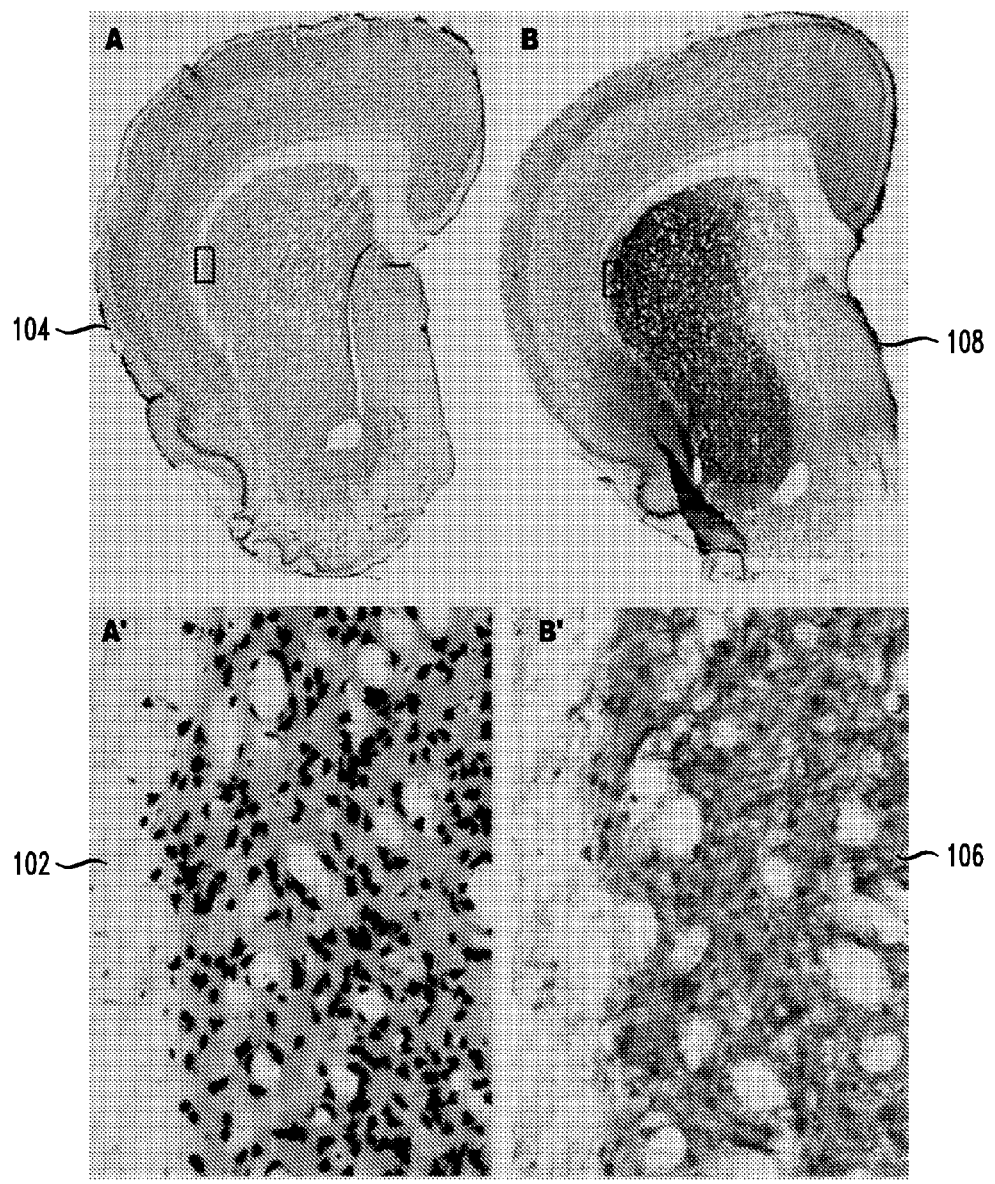
FIG. 1 is a diagram illustrating a typical brain section from a 3-nitropropionic acid (3-NP) treated rat only injected with saline each day and a brain section from a 3-NP treated rat injected with 10 mg/day/rat of Gabadur, according to an embodiment of the present invention.

The present invention will be described herein in the context of mechanisms for targeting protease inhibitors and/or other pharmaceutical compounds in vivo using known pharmaceutical agents as carriers. It should be understood, however, that embodiments of the present invention are not limited to these or any other specific drug delivery mechanisms. Rather, the invention is more generally applicable to techniques for targeting a pharmaceutically active compound using, as a carrier, a molecule (or molecules) having greater affinity for a particular site in a living organism's body than for other sites in the organism's body. Also, a carrier molecule may be a lipid-soluble molecule that can bind to lipid-insoluble molecules and transport the lipid-insoluble molecules across membranes. Carrier molecules possess specific sites that interact with the molecules they transport, and the efficiency of carrier molecules may be modified.

Analogs of existing pharmaceuticals may be explored as a source for their potential as carriers of pharmaceutically active compounds of all types for their therapeutic intervention into various forms of pathological conditions, particularly degenerative diseases, including, but not limited to, muscle and nerve degeneration, hearing loss (for example, tinnitus), inflammatory diseases, cardiovascular disorders, pain, epilepsy, bone resorption, cancer and Huntington's disease. The analogs of existing pharmaceutical agents may or may not possess more or less therapeutic activity for which it was originally designed. However by linking them to new pharmaceutically active agents (for example, protease inhibitors), their overall metabolic activity can be extensively modified.

Drug targeting may be defined in a broadest sense as optimizing a drug's (or other pharmaceutical agent's) therapeutic index by substantially localizing its pharmacological activity to the site of action. This is distinguishable from the basic targeting concept, wherein a specific drug receptor is the target and the objective is to improve fit, affinity, and/or binding to a specific receptor that will ultimately trigger the pharmacological activity.

Successful drug targeting is a very complicated problem, one that has been the subject of intense research in recent history. There are several important factors to be considered in designing drug targeting of any kind. These factors include, but are not limited to, the nature of biological and cellular membranes, distribution and presence of drug receptors, as well as the enzymes responsible for drug metabolism, time-plasma concentration profiles and local blood flow. Each of these factors requires intensive study, including significant clinical trials, etc., and therefore the emergence of novel drug targeting methodologies has traditionally been considerably delayed.

One or more embodiments of the present invention provide a mechanism for targeting pharmaceutically active compounds, such as, for example, protease inhibitors, which exploits the fact that specific pharmaceutical agents, when administered, are already known to be selectively taken up primarily in certain tissues in vivo. In general terms, protease inhibitors are molecules that inhibit the function of proteases. Further, protease inhibitors are a class of medication used to treat or prevent infection by viruses, including those that transmit human immuno-deficient virus (HIV) infections. Protease inhibitors prevent viral replication by inhibiting the activity of HIV protease used by the viruses to cleave nascent proteins for final assembly of new virons.

Thus, by tagging a new pharmaceutically active compound (for example, protease inhibitor) onto a known pharmaceutical agent acting as a carrier, the pharmaceutically active compound can be beneficially targeted to a desired site of the body (for example, tissue, organ, organelle, etc.). The resulting compound preferably has the formula:

$$B\text{-}L\text{-}A \qquad (1)$$

where B in formula (1) above represents the residue or an analog of a small synthetic molecule, preferably one that is approved for human use, having a greater affinity for a particular site in a patient's body than for other sites in the patient's body, L represents a direct covalent bond or a linking group which covalently binds A and B, and A represents the residue or an analog of a pharmaceutically active compound. In this manner, since known pharmaceutical agents or their analogs are preferably used as carriers, or targeting agents, the invention can advantageously speed the emergence of effective drug targeting methodologies.

In another aspect of the invention, a method of targeting a pharmaceutically active compound (for example, protease inhibitor) to a particular site in a patient's body is provided, the method comprising the steps of coupling the pharmaceutically active compound to a small synthetic molecule having greater affinity for the particular site than for other sites in the patient's body, and administering a therapeutically effective amount of the coupled product to the patient. In accordance with an exemplary embodiment of the invention, the coupled product is administered orally, intravenously, intramuscularly, or intra-tympanically to the patient.

Having a greater affinity may be defined herein as binding and/or being internalized into a cell more easily at one site of an organism's body compared to another site(s) in the organism's body. Greater affinity may be measured, in one aspect, as increased cellular uptake at lower dosage levels. For example, carnitine mediates the transport of medium/long-chain fatty acids across mitochondrial membranes, thereby facilitating their oxidation with subsequent energy production. Because of these key functions, carnitine is concentrated in tissues that utilize fatty acids as their primary dietary fuel, such as skeletal and cardiac muscle. When linked to carnitine or aminocarnitine, protease inhibitors are taken up more than 100 times more effectively in skeletal muscle tissue than in other tissue types. Another example is taurine, a chemical naturally occurring in blood, brain and other nervous tissue, bile, as well as other tissues. When protease inhibitors are linked to cysteic acid (which utilizes taurine transport mechanisms), studies indicate that they are taken up in nervous tissue about ten times more effectively.

A therapeutically effective amount of the compound in formula (1) above is preferably administered to a patient as at least part of an effective treatment regimen. As used herein, a therapeutically effective amount of the compound may be defined as the amount of compound which, when administered to a patient for the treatment of a certain pathological condition, results in diminishing symptoms of the condition, up to a certain toxicity level. Preferably, the amount of compound administered to a patient is about 0.1 milligrams per kilogram (mg/kg) to about 50 mg/kg, although the invention is not limited to any specific dosage amount.

As previously stated, the pharmaceutically active compound which is attached (for example, linked, bonded, etc.) to the pharmaceutically acceptable carrier is a protease inhibitor, although the invention is not limited to this class of pharmaceutically active compounds. Protease inhibitors are molecules that inhibit the function of proteases (also referred to as peptidases, proteinases or proteolytic enzymes). Proteases are enzymes that selectively and specifically break certain peptide bonds between amino acids of proteins and are an essential and ubiquitous mechanism for the function of a myriad of physiological processes. Inhibition of proteolytic activity is generally employed for two primary purposes, namely, for the prevention of unwanted degradation of intracellular proteins required for structural or regulatory functions.

Four main classes of proteolytic enzymes have been routinely utilized to describe proteases, namely, cysteine proteases (which include papain, calpain and lysosomal cathepsins), serine proteases (which include trypsin, chymotrypsin and elastase), aspartic proteases (which include pepsin and rennin) and metallo-proteases (which include thermolysin and carboxypeptidase).

Protease inhibitors presently being tested for therapeutic use in humans include, but are not limited to, Brecanavir (GW640385 or VX-385), manufactured by GlaxoSmithKline and Vertex, Darunavir (TMC114), manufactured by Tibotec, and PPL-100, manufactured by Procyon Biopharma.

By way of example only, and without loss of generality, in accordance with one exemplary embodiment of the invention, bisphosphonates are employed as a carrier or targeting agent for a pharmaceutically active compound, such as, for example, a protease inhibitor, in order to delay and/or treat degenerative bone diseases. Bisphosphonates are a class of drugs known for their ability to help prevent bone destruction resulting from bone diseases, including, but not limited to, osteoporosis, bone cancer, Paget's disease, hypercalcemia and bone metastases. Bisphosphonates share a basic phosphate-carbon-phosphate core and bind strongly to calcium containing molecules such as hydroxyapatite. Thus, bisphosphonates have a strong affinity for bone tissue. A generic bisphosphonate structure is shown below, where the symbol R denotes any group of atoms.

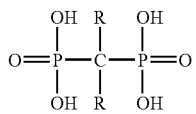

Some common bisphosphonates contain a functional group on R which is suitable for use as a carrier for protease inhibitor attachment. These include, for example, etidronate (Didronel®, a registered trademark of Procter & Gamble Pharmaceuticals), pamidronate (Aredia®, a registered trademark of Novartis Pharmaceutical Corp.), alendronate (Fosamax®, a registered trademark of Merck & Co., Inc.), risedronate (Actonel®, a registered trademark of Procter & Gamble Pharmaceuticals), zoledronate (Zometa®, a registered trademark of Novartis Pharmaceutical Corp.) and ibandronate (Boniva®, a registered trademark of Roche Therapeutics Inc.). Covalent attachment of protease inhibitors, or other pharmaceutically active compounds, to such bisphosphonates could delay and/or treat the degenerative process by inhibiting an involved protease.

In accordance with another exemplary embodiment of the invention, a Pregabalin analog is employed as a carrier for a protease inhibitor, or alternative pharmaceutically active compound. Pregabalin (Lyrica®, a registered trademark of Pfizer Inc.) is a known anticonvulsant drug indicated as an add-on therapy for partial onset seizures often used in the treatment epilepsy and for certain types of neuropathic pain. Covalent linkage of a specific protease inhibitor (for example, leucyl-argininal) to a pregabalin analog would assist in bringing that compound across the blood-brain barrier (BBB) for treatment of typical neurodegenerative diseases (for example, Huntington's disease).

In accordance with an illustrative embodiment of the present invention, a compound is provided, wherein the compound includes formula (1) above, and wherein B represents a residue of a compound of the formula (2):

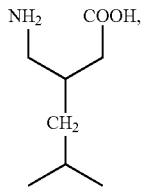

(2)

L represents a direct bond or a linking group, and A represents the residue of a protease inhibitor from the class of caspase inhibitors, calpain inhibitors, matrix metalloproteinase inhibitors, and proteosome inhibitors.

In accordance with another illustrative embodiment of the invention, a compound is provided, wherein the compound includes formula (1) above, and wherein B represents an analog of a compound Pregabalin [(S)-(+)-3 isobutylgaba] of the formula (2) above, L represents a linking compound (for example, a molecule that links A and L through peptide bond or amide linkage), and A represents a residue of calpain inhibitor.

In accordance with another exemplary embodiment of the invention, a compound is provided, wherein the compound includes formula (1), and wherein the compound is a protease inhibitor (which may, for example, include a functional group such as, for example, free aldehyde or diethyl acetal):

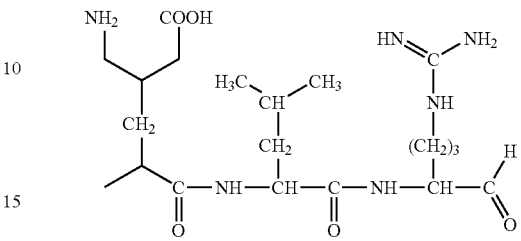

In accordance with this exemplary embodiment of the invention, a method of making the compound is provided herein, wherein the method includes the step of cleaving a compound of the formula (3) called leupeptin or its diethyl acetal with the protease thermolysin:

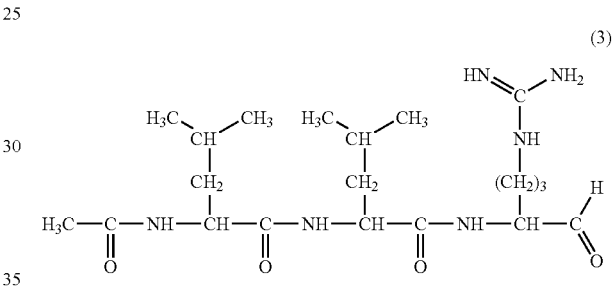

(3)

to obtain the compound, of the formula (4) or its diethyl acetal:

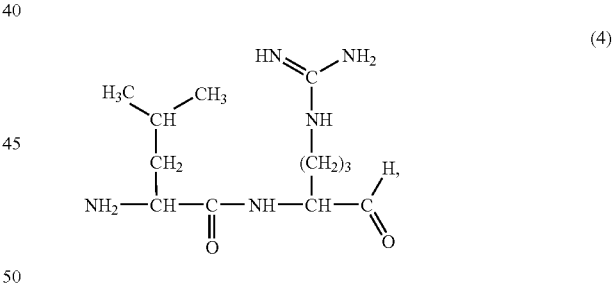

(4)

and the step of coupling the compound as shown in formula (4) above with a compound of the formula (5) by use of linking group L:

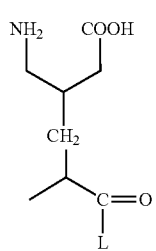

(5)

In accordance with another exemplary embodiment of the invention, a compound is provided, wherein the compound includes formula (1) above, and wherein the compound is:

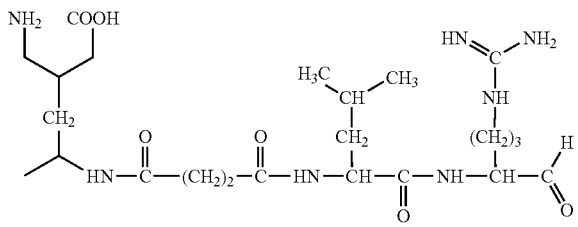

In accordance with this exemplary embodiment of the invention, a method of making the compound is provided herein, the method comprising the steps of: (i) cleaving n-acetylleucine off a compound of the formula (3) above by use of the enzyme Thermolysin, to obtain a compound of the formula (4) above, and (ii) coupling the compound shown in formula (4) above with a compound of a formula (6) below:

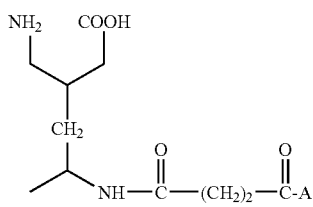

(6)

in the presence of succinic anhydride and forming a diamide compound, where A in formula (6) above represents the residue of a protease inhibitor, or another pharmaceutically active compound.

In accordance with an exemplary aspect of the present invention, a method of treating a neurodegenerative disorder selected from the group comprising Huntington's disease, amyotrophic lateral sclerosis (ALS, also referred to as Lou Gehrig's disease), Parkinson's disease, Alzheimer's disease, tinnitus, spinal cord injury, head trauma, retinal degeneration, bone resorption and epilepsy is provided, wherein the method includes the step of administering to a patient a therapeutically effective amount thereof of a compound according to the embodiments of the invention described herein above. Administration of treatment may be done, for example, by at least one of orally, intraperitoneally, intravenously, intramuscularly, and intra-tympanically.

In an illustrative embodiment of the present invention, proteolytic processing of mutant Huntingtin protein (Htt) is shown to play a role in the disease progression of Huntington's disease. The calcium activated family of proteases, calpains, has been implicated in the increased proteolysis patterns of Htt and may lead to the toxicity observed in this degenerative disease.

The use of selective calpain inhibitors, in vivo, demonstrates that decreasing calpain activity attenuates the degeneration seen in every applicable case. For example, in animal models of Duchenne muscular dystrophy (DMD), multiple sclerosis, myasthenia gravis, hearing loss and traumatic nerve injury, use of the calpain inhibitor leupeptin has led to therapeutic benefit.

Also, increased calpain activity has been shown to be present in a variety of other neurodegenerative diseases including, for example, ALS, cardiomyopathies, Alzheimer's disease, Parkinson's disease, retinal degeneration, cerebral ischemia, experimental autoimmune encephalomyelitis (EAE), epilepsy, and spinal cord injury. Thus, the broad diversity of calpain involvement legitimately suggests that a common pathway exists in the pathology of these exemplary degenerative diseases and that calpain inhibition may represent a legitimate target for therapeutic intervention.

In an illustrative embodiment of the present invention, a mechanism for calpain-induced neurodegeneration (that is, an exemplary common pathway) may include, for example, the following mechanism:

Trauma and/or Ischemia------>Altered membrane permeability-------->Elevated calcium-------->Calpain activation---------->Widespread degradation of multiple substrates--------->Cellular dysfunction, instability and death.

As described above, delivery of a therapeutic agent to a selective tissue has greater efficiency and lowered toxicity if the agent (for example, protease inhibitor) is targeted to a specific tissue, such as, for example, muscle or nerve. To this end, an exemplary embodiment of the present invention includes chemically linking a specific, small molecule carrier to the active end of a leupeptin molecule. For use with a muscle, the selected carrier may be, for example, carnitine (Myodur), and for use with a nerve, the selected carrier may be, for example, an analog of taurine. Enhanced delivery to the tissue of choice is demonstrated by 150-fold in the case of carnitine and approximately 10-fold in the case of taurine. Both modified forms are deliverable, for example, by an oral route which greatly diminishes degenerative processes such as, for example, DMD and EAE.

Figure 2:
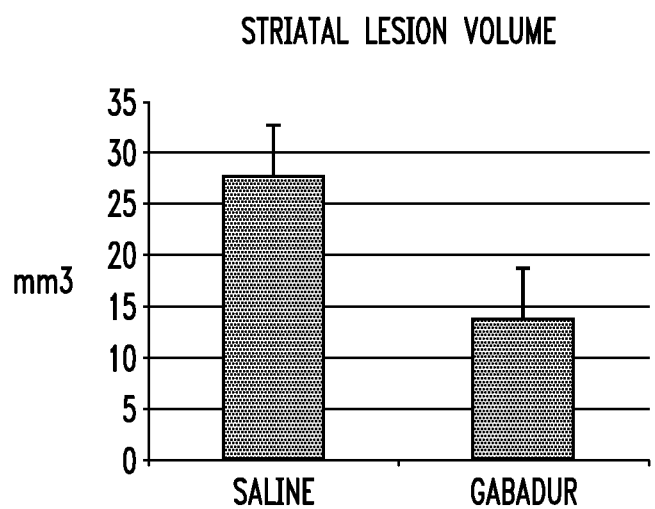
FIG. 2 is a diagram illustrating striatal lesion volume in 3-NP treated rats then treated with saline or Gabadur, according to an embodiment of the present invention.

Because calpain has been demonstrated to play a significant role in the onset of Huntington's disease, an exemplary embodiment of the present invention illustrates the therapeutic potential of using a new calpain inhibitor, Gabadur. These exemplary modified forms of leupeptin with attached carriers enable the inhibitor to cross the blood-brain barrier (BBB) via an oral route. For example, a 3-Nitropropionate model, which has been shown to elicit striatal lesions similar to those observed in HD, may be used. As illustrated in FIG. 1 and FIG. 2 (described below), Gabadur dissolved in buffer and administered intraperitoneally (IP) reduced the striatal lesions usually induced by 3-NP.

The calpain inhibitors are water soluble and can be, as way of example, delivered orally. Calpain inhibitors can also be delivered, for example, intravenously, intramuscularly, or intra-tympanically. Experiments were carried out in rats after infusion of 3-nitropropionate. Observations were made as to whether decreased striatal degeneration subsequently occurred. Endogenous calpain levels were measured, as were calpain-mediated breakdown products of fodrin in brain tissue at various time levels following 3-NPA administration in treated and untreated animals (for example, 3-5 animals in each group).

Administration of 3-nitropropionic acid (3-NP), a succinic dehydrogenase inhibitor which is a mitochondrial toxin, produces the principle features of Huntington's disease in rodents and primates. An exemplary feature is degeneration of striatal medium spiney GABAergic neurons resulting in abnormal movements and cognitive deficits.

Twelve week old Lewis rats weighing 340-370 grams (g) were used in the experiments described herein. 3-NP was dissolved in water and the pH was adjusted to 7.4 with sodium hydroxide. 3-NP was administered at a dose of 50 milligram per kilogram of body weight per day (mg/kg/day) by osmotic mini-pump for 5 days, at which time the animals were sacrificed and brain slices made. Gabadur (pregabalin-leuargal) was dissolved in isotonic buffer and was given by intraperitoneal injection twice a day. Each injection contained enough Gabadur for a dose of 10 milligram per rat per day (mg/rat/day). One injection of Gabadur was administered 12 hours before the mini-pump containing the 3-NP was implemented.

FIG. 1 is a diagram illustrating a typical brain section from a 3-nitropropionic acid (3-NP) treated rat injected only with saline each day and a brain section from a 3-NP treated rat injected with 10 mg/day/rat of Gabadur, according to an embodiment of the present invention. As illustrated by the photomicrographs in FIGS. 1, 102 and 104 depict a typical brain section from a 3-nitropropionic acid treated rat injected only with saline each day. 102 is a 200-fold enlargement of the rectangle shown in 104. 108 is a brain section from a 3-nitropropionic acid treated rat injected with 10 mg/rat/day of Gabadur. 106 is a 200-fold enlargement of the rectangle shown in 108.

The control rats (treated with saline) showed apparent focal degeneration and necrosis with complete loss of cell details and architecture, as well as the appearance of distinct basophilic remnants of nuclei in the striatal area. The Gabadur-treated rats yielded brain slices showing preservation of normal histological structure in about half of the striatal area. Thus, the calpain inhibitor Gabadur, at the 10 mg/rat/day injected dose, was an effective agent for preventing about 50% of the brain damage inflicted by 3-NP.

FIG. 2 is a diagram illustrating striatal lesion volume in 3-NP treated rats then treated with saline or Gabadur, according to an embodiment of the present invention. As illustrated by FIG. 2, striatal volume (measured in cubic millimeters (mm$^3$)) were measured in 3-NP rat models (3-NP treatment of 50 mg/kg/day by mini-pump for five days) for control rats treated with saline and rats treated with 10 mg/rat/day of Gabadur. The Gabadur-treated rats yielded estimated striatal lesion volumes of about half of the striatal lesion volumes of the control rats indicating neuroprotective action of Gabadur. It is to be appreciated by one skilled in the art that administering doses at different schedules may also be implemented herein. For example, a therapeutically effective of Gabadur may include a range of 1 mg/kg/day to 200 mg/kg/day.

In an illustrative embodiment of the present invention, Gabadur is known by the chemical name of [(3S,4S)-3-aminomethyl-4-amino-5-methyl hexanoic acid]-Suc-Leu-Arg-aldehyde diethyl acetal, and is depicted by the structure below. As described herein, Gabadur may be used to treat one or more diseases including, for example, Huntington's disease. The formula of the compound is as follows:

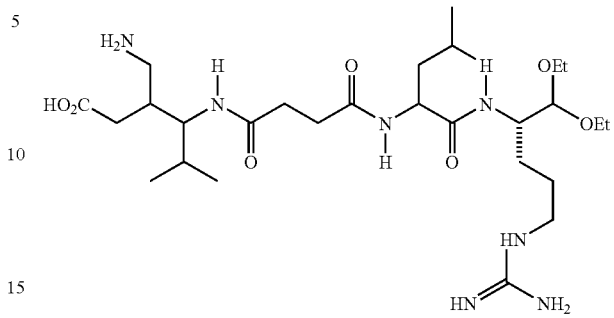

Although illustrative embodiments of the present invention have been described herein with reference to the accompanying drawings, it is to be understood that the invention is not limited to those precise embodiments, and that various other changes and modifications may be made therein by one skilled in the art without departing from the scope of the invention as set forth in the appended claims.

What is claimed is:

1. A compound comprising Gabadur, and wherein Gabadur comprises

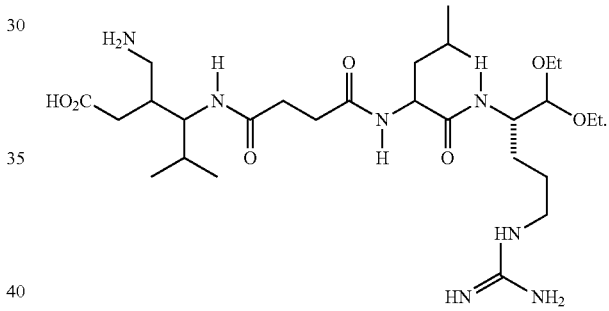

2. A pharmaceutical composition, comprising:
a therapeutically effective amount of the compound according to claim 1; and
a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,729,024 B2 | Page 1 of 1 |
| APPLICATION NO. | : 12/280844 | |
| DATED | : May 20, 2014 | |
| INVENTOR(S) | : Stracher et al. | |

It is certified that error appears in the above-identified patent and that said Letters Patent is hereby corrected as shown below:

In the Claims:

Claim 1, column 10, line 27, please delete "and" before "wherein".

Signed and Sealed this
Fifth Day of August, 2014

Michelle K. Lee
*Deputy Director of the United States Patent and Trademark Office*